United States Patent
Lüscher et al.

(10) Patent No.: US 6,299,590 B1
(45) Date of Patent: Oct. 9, 2001

(54) IMPLANT, AND METHOD AND DEVICE FOR INSERTING THE IMPLANT

(75) Inventors: Patrik Lüscher, Pfäffikon; Erich Wintermantel, Fislisbach, both of (CH)

(73) Assignee: Boston Scientific Corporation, Boston, MA (US)

( * ) Notice: Subject to any disclaimer, the term of this patent is extended or adjusted under 35 U.S.C. 154(b) by 0 days.

(21) Appl. No.: 09/225,682

(22) Filed: Jan. 6, 1999

Related U.S. Application Data (62) Division of application No. 08/776,943, filed on Apr. 21, 1997.

(30) Foreign Application Priority Data

Aug. 17, 1994 (CH) .................................................. 2533/94

(51) Int. Cl.$^7$ ................................................. A61M 21/00
(52) U.S. Cl. ........................... 604/11; 604/502; 604/507; 604/522; 604/150
(58) Field of Search ............................... 606/1, 108, 151, 606/191–200, 213; 604/11, 13, 19, 500, 502, 506, 507, 508, 511, 514–517, 522, 57, 59, 60, 82, 83, 85, 93.07, 150–154

(56) References Cited

U.S. PATENT DOCUMENTS

| | | |
|---|---|---|
| Re. 34,866 | 2/1995 | Kensey et al. . |
| 903,107 | 3/1908 | Ramus . |

(List continued on next page.)

FOREIGN PATENT DOCUMENTS

| | | |
|---|---|---|
| 31 15763 | 11/1982 | (DE) . |
| 0186632 | 7/1986 | (EP) . |
| 0 621 020 | 10/1994 | (EP) . |
| 2 696 636 | 4/1994 | (FR) . |
| 61-161220 | 7/1986 | (JP) . |
| 2-280768 | 11/1990 | (JP) . |
| 2-280769 | 11/1990 | (JP) . |
| 2-280770 | 11/1990 | (JP) . |
| 2-280771 | 11/1990 | (JP) . |
| 4-20348 | 1/1992 | (JP) . |
| 4-197359 | 7/1992 | (JP) . |
| 5-208917 | 8/1993 | (JP) . |
| WO 91/13592 | 9/1991 | (WO) . |
| WO 93/00127 | 1/1993 | (WO) . |
| 5-504695 | 7/1993 | (WO) . |
| WO 94/16632 | 8/1994 | (WO) . |
| WO 97/19643 | 6/1997 | (WO) . |

OTHER PUBLICATIONS

A. Polk et al., "Controlled Release of Albumin from Chitsan–Alginate Microcapsules," Journal of Pharmaceutical Sciences, vol. 83, No. 2 (Feb. 1994), pp. 178–185.

K. Kamath et al., "Biodegradable Hydrogels in Drug Delivery," Advanced Drug Delivery Reviews, 11 (1993), pp. 59–84.

Rüfenacht, D.A. et al., "A Simple Propulsion–Chamber–System for the 16 Gauge Approach"; Neuroradiology (1986) 28:355–358.

Marks, R., et al., "Principles of Weaving"; The Textile Institute Manchester, 1976, pp. 130–135.

*Primary Examiner*—Glenn K. Dawson
(74) *Attorney, Agent, or Firm*—Finnegan, Henderson, Farabow, Garrett & Dunner, L.L.P.

(57) ABSTRACT

A ball-shaped implant made out of a pliable fiber. The fiber is introduced into the body and when it encounters body tissue it folds upon itself to form a ball-shaped implant. A fluid may be placed around the implant either to hold it in place or to add a biologically active agent to the implant. The fiber of the implant may be biodegradable, or hollow and porous to allow for drugs placed inside the fiber to be administered to the body. One end of the fiber may be long enough to extend out of the body for later removal.

60 Claims, 3 Drawing Sheets

U.S. PATENT DOCUMENTS

| | | |
|---|---|---|
| 2,524,195 | 10/1950 | Hoover . |
| 3,431,907 | 3/1969 | Lubet-Moncla . |
| 3,481,335 | 12/1969 | Beutlich . |
| 3,703,174 | 11/1972 | Smith . |
| 3,826,256 | 7/1974 | Smith . |
| 3,906,550 | 9/1975 | Rostoker et al. . |
| 4,159,022 | 6/1979 | Pevsner . |
| 4,237,885 | 12/1980 | Wong et al. . |
| 4,402,308 | 9/1983 | Scott . |
| 4,512,338 | 4/1985 | Balko et al. . |
| 4,551,132 | 11/1985 | Pasztor et al. . |
| 4,712,553 | 12/1987 | MacGregror . |
| 4,820,767 | 4/1989 | Wu . |
| 4,840,622 | 6/1989 | Hardy . |
| 4,932,942 | 6/1990 | Maslanka . |
| 4,950,295 | 8/1990 | Weigum et al. . |
| 4,994,069 | 2/1991 | Ritchart et al. . |
| 5,021,059 | 6/1991 | Kensey et al. . |
| 5,074,840 | 12/1991 | Yoon . |
| 5,100,392 * | 3/1992 | Orth et al. ............................ 604/93 |
| 5,211,627 | 5/1993 | William . |
| 5,250,071 | 10/1993 | Palermo . |
| 5,256,146 | 10/1993 | Ensminger et al. . |
| 5,263,927 | 11/1993 | Shlain . |
| 5,308,342 | 5/1994 | Sepetka et al. . |
| 5,318,524 | 6/1994 | Morse et al. . |
| 5,322,510 | 6/1994 | Lindner et al. . |
| 5,336,263 | 8/1994 | Ersek et al. . |
| 5,374,261 | 12/1994 | Yoon . |
| 5,376,118 | 12/1994 | Kaplan et al. . |
| 5,443,454 | 8/1995 | Tanabe et al. . |
| 5,454,833 | 10/1995 | Boussignac et al. . |
| 5,514,158 | 5/1996 | Kanesaka . |
| 5,522,795 | 6/1996 | Green et al. . |
| 5,522,822 | 6/1996 | Phelps et al. . |
| 5,545,169 | 8/1996 | Yarger . |
| 5,571,189 | 11/1996 | Kuslich . |
| 5,575,815 | 11/1996 | Slepian et al. . |
| 5,591,224 | 1/1997 | Schwartz et al. . |
| 5,614,204 | 3/1997 | Cochrum . |
| 5,660,854 | 8/1997 | Haynes et al. . |
| 5,667,778 | 9/1997 | Atala . |
| 5,690,666 * | 11/1997 | Berenstein et al. ............... 606/191 |
| 5,766,160 * | 6/1998 | Samson et al. ..................... 606/1 |
| 5,954,682 | 9/1999 | Petrus . |

OTHER PUBLICATIONS

Goto, K., et al., "A New Technique for Embolization of Cerebral Arteriovenous Malformations and Dural Arteriovenous Fistulae"; Neuroradiology (1991) 33[Suppl] :193–194.

Harper, Marion, et al., "Isobutyl 2–cyanoacrylate as an Osseous Adhesive in the Repair of Osteochondral Fractures"; Journal of Biomedical Materials Research, vol. 17, pp. 167–177 (1983).

Serbinenko, F.A., M.D., "Balloon Catheterization and Occlusion of Major Cerebral Vessels"; J. Neurosurg, vol. 41, Aug. 1974, pp. 125–145.

Taki et al., "The Eleventh General Meeting of Japan Biomaterial Society Collection of Scripts for Presentation"; Oct. 1989, At Kyoto University, Chief of the 11th Meeting: Takao Yamamuro.

Ayumi, Igaku No. [SIC], "Embolization Technique of Cerebral Arterial Aneurysm Advantages and Disadvantages of Embolization Technique and Surgical Operation"; vol. 153, No. 11, p. 635, Jun. 1990, Ishiyaku Publishers, Inc.

Ayumi, Igaku No. [SIC], "Situtation of New Subspeciality of Neurosurgery"; vol. 154, No. 7, p. 432, Aug. 1990, Ishiyaku Publishers, Inc.

Goto, K., "recent Advances and Future Problems of Interventional Neuroradiology"; Neurosurgeons 9:229–239, Sep. 1990.

Taki, K., "Possibility and Limit of Intravascular Surgery"; Medical Tribune, pp. 46–47, Oct. 1989, Nippon Accel Shubringer Shuppan, K.K.

Bernatchez et al., "Biocompatibility of a New Semisolid Bioerodible Poly(ortho ester) Intended for the Ocular Delivery of 5–fluorouracil"; Journal of Biomedical Materials Research; vol. 28, No. 9, pp. 1037–1046, Sep., 1994.

Bernatchez et al., "Biotolerance of a Semisolid Hydrophobic Biodegradable Poly(ortho ester) for Controlled Drug Delivery"; Journal of Biomedical Materials Research; vol. 27, No. 5, pp. 677–681, May, 1993.

* cited by examiner

IMPLANT, AND METHOD AND DEVICE FOR INSERTING THE IMPLANT

This is a divisional of application Ser. No. 08/776,943, filed Apr. 21, 1997, (pending), the disclosure of which is incorporated herein by reference.

This invention is regarding an implant, the usage of this implant, as well as the device and the method for the application of the implant.

In medicine, implants are known for their different uses, and their numerous types. In general, implants are inserted in their entirety which involves a comparatively large surgical operation thus resulting in a corresponding high strain on the patient.

The basic task of this invention is to create an implant which can be used while exerting minimal strain on the patient and which is distinguished by its vast range of application. With the same purpose, the task of this invention is to create a device for the application of the implant as well as to create a method for the application of the implant.

According to this invention, the implant is characterized by a ball of fiber which is in the form of a three-dimensional, open-pore structure. Such a ball of fiber can be introduced, in optional amounts (in situ) via a small insertion using surgical micro-technology with minimal strain to the patient. A wide variety of possible applications arise particularly from the fact that the size and the shape of the implant are widely variable and can be determined during the operation. For example, the pore-size and the structural characteristics of the implant can be varied by modifying the material characteristics, in particular the fiber. The fiber can be the carrier of biologically active substances and is particularly suitable for controlled medication-release or for the induction of body-tissue. Numerous applications are also envisioned for the fields of dentistry and veterinary medicine.

According to this invention, the device for the application of the implant is characterized by a tube and instruments, which deliver the implants in fiber-shaped form through a distal opening of the tube. Since the device, (according to this invention), leads the implant in fiber-shaped form through the tube and deposits it at this point, an application using surgical micro technology and hence a minimal invasive implantation is possible.

According to a further development of the device, (according to this invention), a fluid-stream is generated by the aforementioned instruments, with which the fiber can be transported through the tube. In addition, the fluid together with the fiber can be delivered through the distal opening of the tube. The fluid, for example, can be designed to serve as a carrier of biologically active substances or as an adhesive for the local stabilization of the fiber which has been deposited within the tissue. Another model is also conceivable, in which the fluid is carried off via an intake-tube which reverses the fluid. The fluid can be a liquid, a suspension, in particular autologous blood, or an electrolyte solution, but also a gas.

According to this invention, this method is characterized by the fact that the implant is brought in fiber-shaped form to the application site, where it is deposited as a three dimensional ball of fiber. This method makes possible the introduction of an implant via an existing or a created small body opening. Therefore this method is possible with minimal strain to the patient. Nevertheless the implant, in its fully developed form, can be a large volume. For example in orthopedic cases, the fiber ball can fill a relatively large tissue defect, in particular a bone defect. The attending physician can precisely determine the length of the fiber and then, for example, measure precisely the administration of medication.

According to a further development of the method, (according to this invention), the fiber is inserted in such away that an end of the fiber protrudes from the insertion site or body-opening respectively. Such an implant can be explanted very easily at any time, in that the fiber is grasped at the protruding end and extracted from the insertion site.

Other characterized and advantages become apparent from the associated patent claims, the description, as well as the figures. Application examples of the invention are explained subsequently using the figures. It is shown:

According to this invention, the device (1) exhibits (according to FIG. 1) a casing (9), which has an interior volume (8) leading into the tube (19) of a hollow needle (17), and which is also connected to tubing (7) through which a fluid (3), in particular a liquid, can be delivered from a container (2) to the interior volume (8). The fluid (3) is delivered by means of a suction pipe (4) and a pump (5) into the tubing (7), in which a valve (6) is used for the dosage of the fluid stream.

Figure 1:
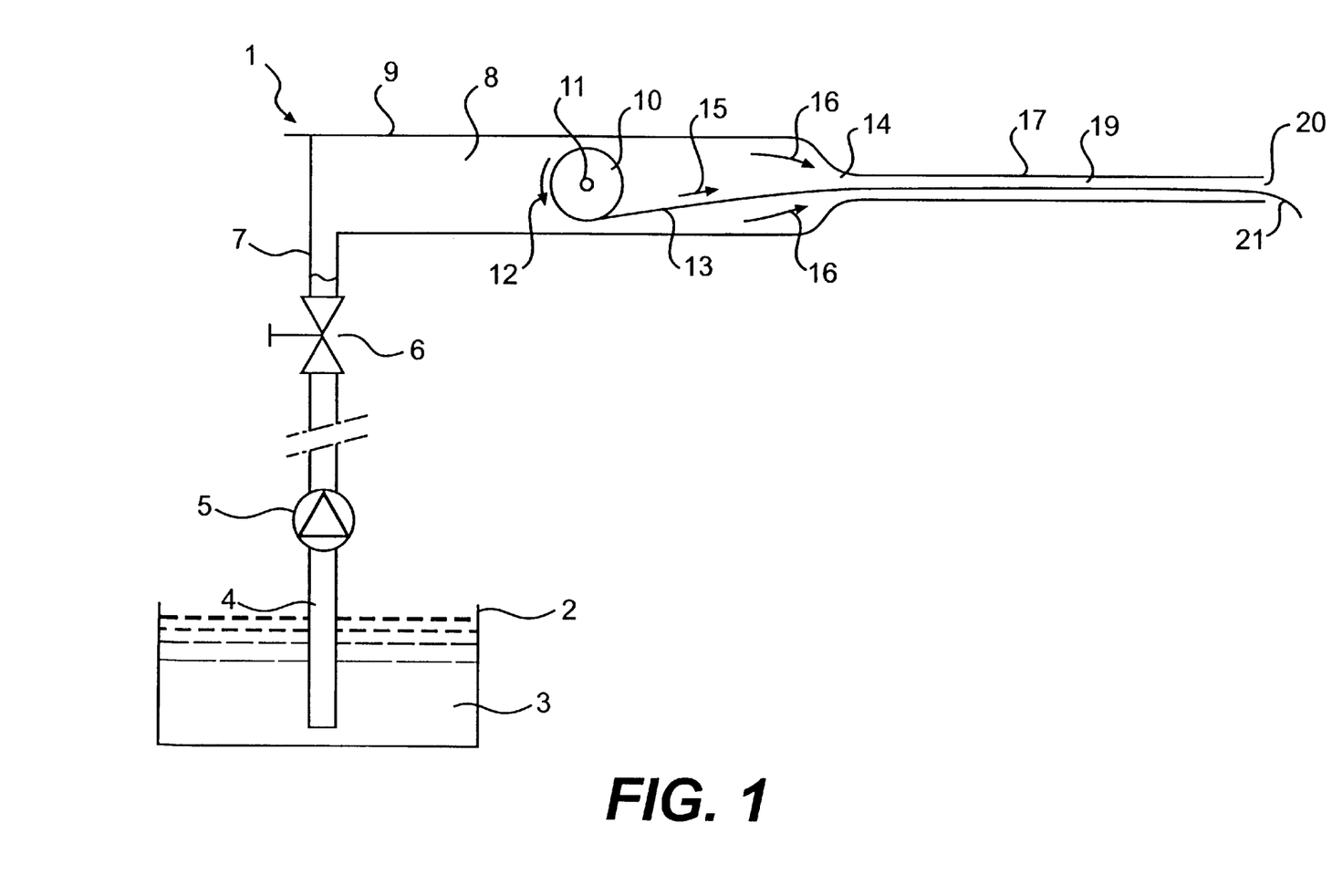
FIG. 1 schematically, a cross-sectional view of a device, (according to this invention), FIGS. 2 and 3 schematically, the application of an implant, (according to this invention), FIG. 4 an implant inserted into tissue FIG. 5 schematically, a cross-sectional view of a variation of the device, (according to this invention)

Inside of the interior volume (8) a fiber bobbin (10) is affixed to an encased axle (11) in such a way that is turns in the direction of the arrow (12. The bobbin (10) is arranged in such a way, that a fiber, which is would up on it, can be unwound in direction of the arrow (15) into the tube (19) of the hollow needle (17). Hereby, the fiber (13) is inserted into a proximal opening (14) of the tube (19) and leaves the tube through a distal opening (20). Another type is also conceivable, according to which the bobbin (10) is affixed outside of the casing (9). Further types are conceivable, in which the bobbin (10) is affixed substituted by another suitable supply device. Finally, types are conceivable, in which the fiber (13) is shorter, or not significantly longer than the tube (19), so that a bobbin (10) or suchlike in not required. The tube (19) is designed is such a way, that the fiber (13) can glide within the tube (19) without any significant friction. In addition, fluid streams from the interior volume (8) in the direction of the arrow (16) into the proximal opening (14) and into the tube (19), where it flows through the tube (19) thereby transporting the fiber (13). The speed of the transport of the fiber (13) in the tube (19) can be increased in particular through the increase of the fluid pressure in the chamber (8). The transport of the fiber can be suspended with an interruption of the fluid-stream at the valve (6). Finally it is possible, that the entire piece of fiber can be delivered to the outside through the distal opening (20).

Figure 2:
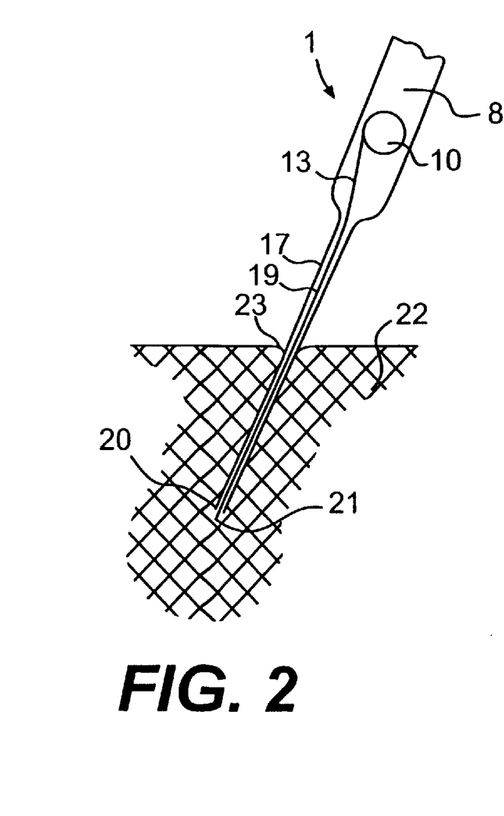
Figures 3, 4:
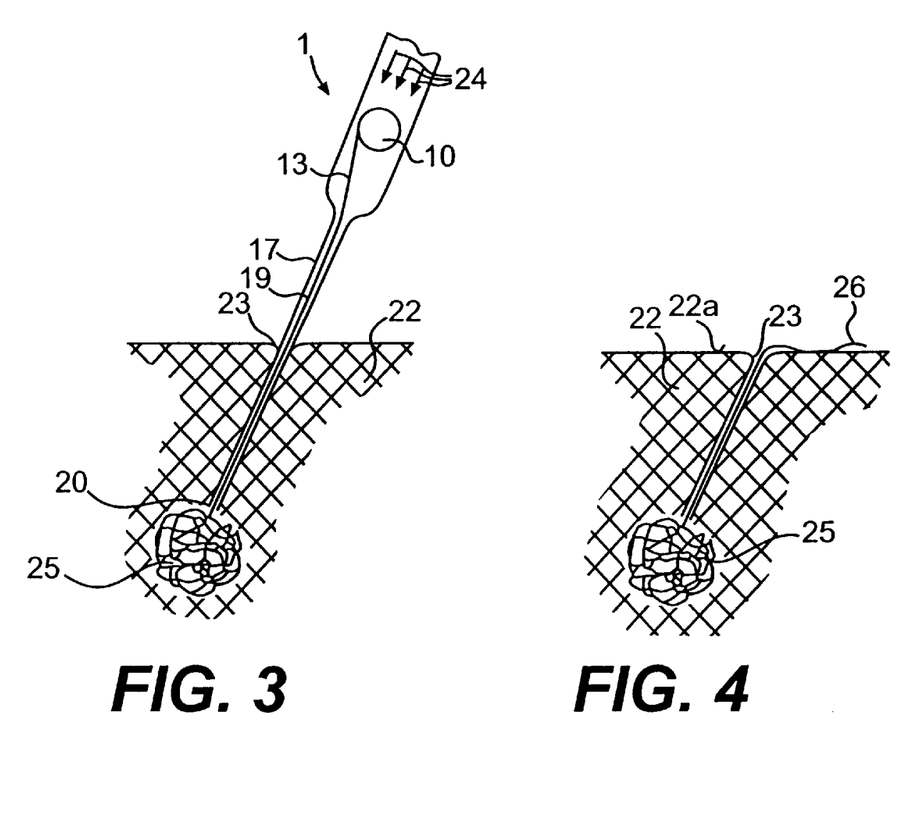

The tube (19) of the hollow needle (17) is designed in such a way that its distal opening (20), (according to FIG. 2), can be pushed through an insertion-opening (23) to a desired site in the tissue (22) or to any other site of the patient's body. When, by adjusting the valve (6), fluid (3) is introduced into the interior volume of this precisely positioned device (1), then this fluid streams in the direction of the arrow (24) (FIG. 3) towards the proximal opening (14) of the tube (19) and into the tube (19). The fiber is unwinding from the bobbin (10), as the fluid transports the fiber (13) towards the distal opening (20) and finally to the outside. The end (21) of the fiber (13), which emerges from the distal opening (20), experiences resistance once it is within the tissue (22). Consequently the following fiber sections are bent and are finally deposited in a ball of fiber (25), (as FIG. 3 demonstrates). Hereby it is essential, that the fiber (13) is lead into the tube (19) near to the opening (20) and can be pushed to the outside.

In this case the fiber (13) is understood to be are interconnected structure with an essentially round cross section, which is very small in relation to its length. The fiber can also be a hollow fiber and/or porous, which means that the fiber is permeable from the inside to the outside, and contains medication. Particularly suitable materials are inorganic gels, for example materials on a silicon-oxide base or calcium-phosphate base, or gels made of synthetic or natural polymers, for example polyorthoester, or natural polymers, for example collagen or heparin. Other applications are conceivable, in which a fiber made of autologous blood components, for example a fibrin-thrombocytes fiber, a metal fiber, or a composite fiber made of several materials are particularly suitable.

The fiber (13) is designed in such a way, that the fiber is, as described above, pliable and foldable. Preferably the fiber exhibits the same diameter throughout its entire length. Yet it is also conceivable that the diameter changes regularly along the fiber.

Preferably the fiber (13) together with the fluid (3) is discharged at the distal opening, so that the ball (25) is surrounded by injected fluid. In the case of a ball (25), which is shaped in such a way, the fiber and the fluid (3) can be both carriers of biologically active substances or particles, for example cells. However the fluid (3) can also be an adhesive, for example a fibrin adhesive, which stabilizes the structure of the ball (25).

By choosing a suitable fiber and fluid, the characteristics of the ball (25) are thus very variable. Futhermore, the size and the structure of the ball (25) can be varied by the length of the fiber and the application technique. Therefore the form and the size of the ball of fiber (25) can be large determined during the operation. The size of the pores as well as the structural characteristics of the ball (25) can also be manipulated to a large extent. The choice of the material characteristics of the fiber (13), the fluid (3), as well as the application technique makes this particularly feasible.

The fluid (3) can be a liquid or a gas. If a gas is selected for the fluid (3), the container has to be accordingly designed as a gas container. In this case a pump (5) is generally not necessary. The choice of the fluid (3) is determined by the intended application. Autologous blood, autologous serum or blood fractions, we well as electrolyte solution are particularly suitable as fluids (3). If the fluid (3) is supposed to stabilize the ball (25), a fibrin adhesive, which can be made of blood, is particularly suitable. A suspension, for example a bone powder or micro spheres or cell suspension, for example bone marrow cells, can serve as the fluid (3) in the case of tissue induction. If the fluid (3) is a gas, then nitrogen is particularly suitable.

The preceding explanations should clarified that the implant, according to this invention, possesses a wide scope of application within medicine as well as within veterinary medicine. In the following several advantageous application possibilities will be discussed.

An essential application of the implant (25), (according to this invention), is the induction of body tissue in cases of tissue engineering. The fiber (13) and/or the fluid (3) can be carriers of cells or cell suspension, which after the formation of the ball of fiber (25) develop new tissue or induce the generation of tissue. The generation of bone tissue in cases of bone defects or in cases of gaps between endoprosthesis and bones is particularly envisioned. Likewise the implantation of a ball (25) can induce bone tissue in cases of vertebra- or joint-fusion, or dentistry. Further applications of the tissue induction are the induction of callus in a case of a bone fracture, as well as tissue induction in plastic surgery, for example induction of connective tissue, cartilage tissue, or endothelium.

Apart from the aforementioned applications for tissue induction, the release of systematically acting medicine or locally acting substances is also possible. Locally acting medications are in particular antibiotics or cytotoxines for the treatment of cancer. According to this invention the implant distinguishes itself particularly by the fine measurability of the acting substances. Even very small amounts of the substance can be precisely determined by choosing the length of the fiber (13). In addition the relates kinetics can be determined by choosing the density of the ball (25). A dense ball (25) can dispense an acting substance more slowly than a loose ball (25). In addition a multi-level release of active agents is possible.

The fiber (13) can also function as a cell carrier, for example a carrier for encysted xenogeneic cells, for example Langerhans cells, nerve cells, or genetically altered cells.

According to this invention a further application for the implant is the therapeutic embolization of, for example hemangioma. Hereby the fiber is inserted into the central vessel of the hemangioma. The very strongly thrombogenic ball of fiber (25) clogs the blood supply of the hemangioma.

A further application for the implant, (according to this invention), is the controlled application of active agents on mucous membranes. For this purpose, a fiber which clings to mucous membranes is brought onto the mucous membranes with the device, (according to this invention, where it releases active agents, which are contained within the fiber, into the mucous membranes.

Therefore according to this invention the implant, in the essential applications, is not "carrying weight" and metabolically inductive.

The fiber (13) can be delivered into the tissue (23) in such a way, that the fiber lies completely within the tissue. However if an explanation of the ball of fiber (25) or an injection or an infusion of medication is intended, then it becomes necessary to position the posterior end (26) of the fiber (13) (according to FIG. 4) in such a way that it protrudes from the puncture site (23). For example the end (26) can be affixed with a piece of adhesive tape (not shown here) on the outer site of the tissue (22a). In the case of an explantation, the fiber (13) is extracted from its end (26) out of the tissue (22). A surgical operation, which would be detrimental to the patient, is hereby not necessary.

Figure 5:
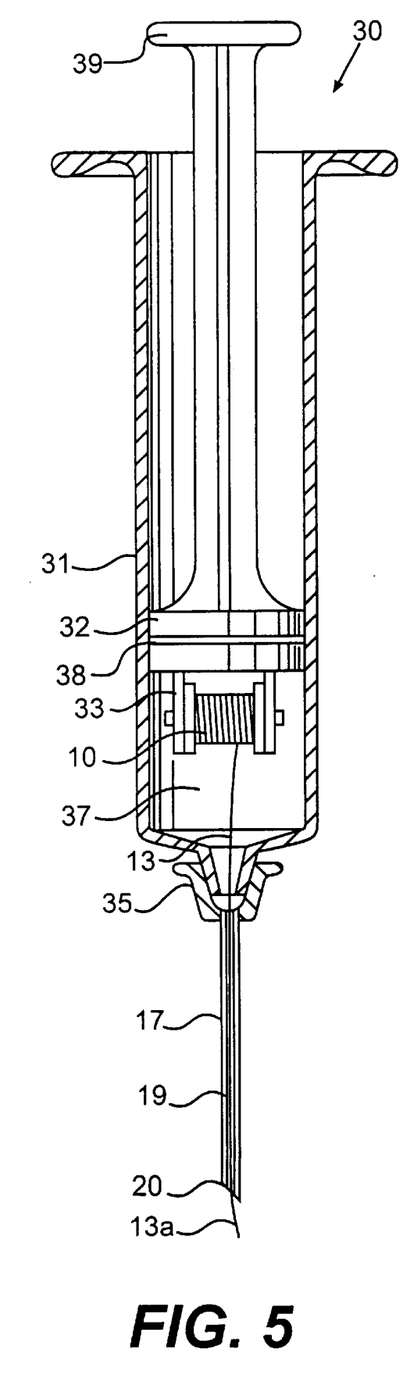

According to the type shown in FIG. 5, the device for the application of the implant is designed as a syringe (30). In particular this is a disposable syringe which is characterized by a casing (31) and a plunger (32) with a gasket (38). The plunger (32) can be moved with a grip (39) within the casing in the usual way. A mounting (33) for the bobbin of fiber (10), on which the fiber (13) is wound on, is positioned on the anterior end of the plunger. Before using the syringe (30), the anterior end (13a) of the fiber (13) should be preferably inserted at least partially into the tube (19) of the hollow needle (17). The hollow needle can be signed like a usual cannula, and is equipped with a snap-on part (35). The hollow space (37) of the syringe (30) contains an aforementioned fluid. When the plunger (32), (lay-out according to FIG. 5), is moved towards the left, the fluid streams under the appropriate pressure into the tube (19), thereby moving along the fiber (13), which has been previously inserted into the tube (19), and unwinding it from a rotating bobbin. The implant is formed within the tissue at the distal end of the hollow needle, as described above.

Other models are also conceivable in which no fluid is used for transporting the fiber (13) through the tube (19). For example the means for the transport can be a propelled bobbin (not shown here) which is positioned at the distal end of the hollow needle (17) and moves the fiber.

Figure 6:
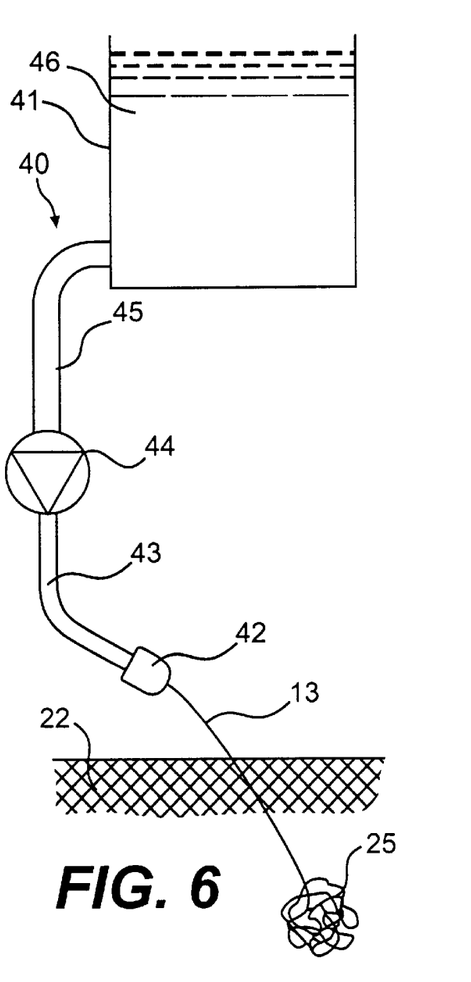
FIG. 6 schematically, an implant with a connected injector.
Figure 7:
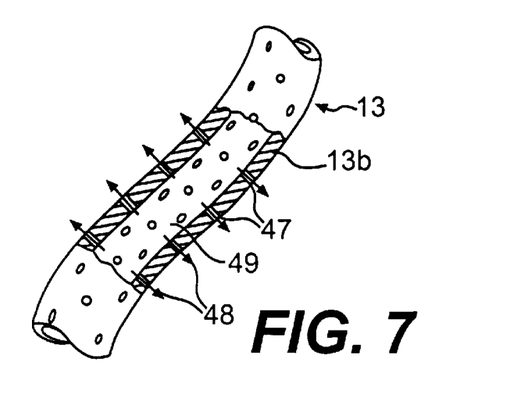
FIG. 7 a section of the fiber in an enlarged scale.

Once an implant (25) has been applied within a tissue, an injector (40) can be connected with an adapter 42 to a protruding end of the fiber (13) (according to FIG. 6). The injector (40) exhibits a reservoir (41) with an active agent (46), a suction tube (45), a pump (44), as well as an inlet tube (43). When the pump (44) is running, an active agent, in particular medication, is lead from the reservoir to the fiber (13). If the fiber (13), (according to FIG. 7), is a hollow fiber with passage openings (47) or pores, hence permeable from the inside to the outside, then the active agent (46) that reaches the hollow space (49) (FIG. 7) of the fiber, can be released through the wall (13b) in the direction of the arrows (48) into the tissue (22) or a body opening. Thereby a precisely measured and directed release of the active agent can be achieved. Likewise in this case the implant can be removed after the treatment.

What is claimed is:

1. A system for introducing a biologically active agent into a body, comprising:
   a source of the biologically active agent; and
   an implant including an elongate fiber, the elongate fiber being separate from the source and having a generally ball shaped portion and an end portion configured to be placed in fluid communication with the source to supply the biologically active agent to the ball shaped portion, the fiber being porous so that the biologically active agent is capable of being released from the fiber.

2. The system of claim 1, wherein the fiber includes a hollow portion for containing the biologically active agent.

3. The system of claim 1, wherein the fiber lacks interweaving with other fibers.

4. The system of claim 1, wherein the fiber is unbiased such that bends in the generally ball shaped portion can be formed as movement of the fiber is resisted.

5. The system of claim 1, wherein the fiber has a pliability such that when the fiber is moved in contact with body tissue, the tissue resists movement of the fiber and following portions of the fiber bend to form the generally ball shaped implant.

6. A system for introducing a biologically active agent into a body, comprising:
   a source of the biologically active agent; and
   an implant including an elongate fiber having a generally ball shaped portion and an end portion in fluid communication with the source to supply the biologically active agent to the ball shaped portion, the fiber being porous so that the biologically active agent is capable of being released from the fiber,
   wherein the source includes a reservoir for storing the biologically active agent and a pump for pumping the biologically active agent from the reservoir to the end portion of the fiber.

7. An implantation system comprising:
   a hollow member having a proximal end portion, a distal end portion for insertion into a body, an opening in the distal end portion, and an inner passageway extending from the proximal end portion to the opening in the distal end portion, wherein the hollow member is a hollow needle; and
   an elongate fiber movable in the inner passageway and through the opening of the hollow member, the fiber being formed of a pliable material so that the fiber bends to form a generally ball shaped implant when the fiber contacts body tissue,
   wherein the fiber is unbiased such that each bend in the ball shaped implant can be formed as movement of the fiber is resisted, the fiber lacks interweaving with other fibers, and the fiber lacks an inner lumen.

8. An implantation system comprising:
   a hollow member having a proximal end portion, a distal end portion for insertion into a body, an opening in the distal end portion, and an inner passageway extending from the proximal end portion to the opening in the distal end portion;
   an elongate fiber movable in the inner passageway and through the opening of the hollow member, the fiber lacking interweaving with other fibers and being formed of a pliable material so that the fiber bends to form a generally ball shaped implant when the fiber contacts body tissue;
   a housing at the proximal end portion of the hollow member, at least a portion of the fiber being stored in the housing prior to formation of the implant; and
   a rotatable bobbin in the housing, the fiber being wound around the bobbin.

9. An implantation system comprising:
   a hollow member having a proximal end portion, a distal end portion for insertion into a body, an opening in the distal end portion, and an inner passageway extending from the proximal end portion to the opening in the distal end portion; and
   an elongate fiber movable in the inner passageway and through the opening of the hollow member, the fiber lacking interweaving with other fibers and being formed of a pliable material so that the fiber bends to form a generally ball shaped implant when the fiber contacts body tissue,
   wherein the fiber is formed of a material including alginate.

10. An implantation system comprising:
   a hollow member having a proximal end portion, a distal end portion for insertion into a body, an opening in the distal end portion, and an inner passageway extending from the proximal end portion to the opening in the distal end portion; and
   an elongate fiber movable in the inner passageway and through the opening of the hollow member, the fiber being formed of a pliable material so that the fiber bends to form a generally ball shaped implant when the fiber contacts body tissue,
   wherein the fiber lacks interweaving with other fibers, the fiber has a pliability such that when the fiber is moved in contact with body tissue, the tissue resists movement of the fiber and following portions of the fiber bend to form the generally ball shaped implant, and the fiber is unbiased such that each bend in the ball shaped implant can be formed as movement of the fiber is resisted, and
   wherein the fiber is porous.

11. The system of claim 10, wherein the fiber lacks an inner lumen.

12. An implantation system comprising:
a hollow member having a proximal end portion, a distal end portion for insertion into a body, an opening in the distal end portion, and an inner passageway extending from the proximal end portion to the opening in the distal end portion; and
an elongate fiber movable in the inner passageway and through the opening of the hollow member, the fiber being formed of a pliable material so that the fiber bends to form a generally ball shaped implant when the fiber contacts body tissue,
wherein the fiber lacks interweaving with other fibers, the fiber has a pliability such that when the fiber is moved in contact with body tissue, the tissue resists movement of the fiber and following portions of the fiber bend to form the generally ball shaped implant, and the fiber is unbiased such that each bend in the ball shaped implant can be formed as movement of the fiber is resisted,
wherein the fiber includes a drug capable of being released when the fiber is implanted in the body, and
wherein the fiber lacks preformed coiling and the fiber lacks preformed braiding.

13. An implantation system comprising:
a hollow member having a proximal end portion, a distal end portion for insertion into a body, an opening in the distal end portion, and an inner passageway extending from the proximal end portion to the opening in the distal end portion; and
an elongate fiber movable in the inner passageway and through the opening of the hollow member, the fiber being formed of a pliable material so that the fiber bends to form a generally ball shaped implant when the fiber contacts body tissue,
wherein the fiber carries one of cells and a cell suspension capable of being released when the fiber is implanted in the body.

14. A method of forming an implant in a body, comprising:
inserting a hollow member in the body, the hollow member having an inner passageway leading to an opening in the hollow member;
moving a pliable fiber through the inner passageway in the hollow member so that the fiber exits the opening in the hollow member, the fiber lacking interweaving with other fibers; and
bending the fiber in a plurality of locations along the length thereof to form a generally ball shaped implant, wherein the bending of the fiber includes
contacting an initial portion of the fiber against tissue in the body, and
resisting movement of the fiber with the tissue so that following portions of the fiber bend to form the generally ball shaped implant,
wherein the fiber is unbiased such that each bend in the generally ball shaped implant is formed as movement of the fiber is resisted, and
wherein the fiber lacks preformed coiling and the fiber lacks preformed braiding.

15. The method of claim 14, further comprising storing at least a portion of the fiber in the inner passageway of the hollow member.

16. The method of claim 14, wherein a housing is at a proximal end portion of the hollow member, and wherein the method further comprises storing at least a portion of the fiber in the housing.

17. The method of claim 14, further comprising releasing a drug from the generally ball shaped implant.

18. The method of claim 14, further comprising allowing an end portion of fiber to extend from the generally ball shaped implant to a location outside of the body and pulling the end portion to remove the implant from the body.

19. The method of claim 14, further comprising forming the generally ball shaped implant in a blood vessel to create an embolism.

20. The method of claim 14, wherein each bend in the generally ball shaped implant is formed as a result of the tissue resisting movement of the fiber.

21. A method of forming an implant in a body, comprising:
inserting a hollow member in the body, the hollow member having an inner passageway leading to an opening in the hollow member;
flowing fluid through the inner passageway so that the fluid carries the fiber through the opening in the hollow member; and
bending the fiber in a plurality of locations along the length thereof to form a generally ball shaped implant, wherein the bending of the fiber includes
contacting an initial portion of the fiber against tissue in the body, and
resisting movement of the fiber with the tissue so that following portions of the fiber bend to form the generally ball shaped implant,
wherein the fiber lacks preformed coiling and the fiber lacks preformed braiding.

22. A method of forming an implant in a body, comprising:
inserting a hollow member in the body, the hollow member having an inner passageway leading to an opening in the hollow member;
moving a pliable fiber through the inner passageway in the hollow member so that the fiber exits the opening in the hollow member;
flowing fluid through the inner passageway so that the fluid carries the fiber through the opening in the hollow member; and
bending the fiber in a plurality of locations along the length thereof to form a generally ball shaped implant, wherein the bending of the fiber includes
contacting an initial portion of the fiber against tissue in the body, and
resisting movement of the fiber with the tissue so that following portions of the fiber bend to form the generally ball shaped implant,
wherein the fluid is an adhesive, and wherein the method further comprises stabilizing the generally ball shaped implant with the adhesive.

23. A method of forming an implant in a body, comprising:
inserting a hollow member in the body, the hollow member having an inner passageway leading to an opening in the hollow member;
moving a pliable fiber through the inner passageway in the hollow member so that the fiber exits the opening in the hollow member;
flowing fluid through the inner passageway so that the fluid carries the fiber through the opening in the hollow member; and
bending the fiber in a plurality of locations along the length thereof to form a generally ball shaped implant, wherein the bending of the fiber includes contacting an initial portion of the fiber against tissue in the body, and resisting movement of the fiber with the tissue so that following portions of the fiber bend to form the generally ball shaped implant, wherein the fluid includes one of a biologically active substance, cells, and a cell suspension, and wherein the method further comprises flowing the fluid in the body via the opening in the hollow member.

24. A method of forming an implant in a body, comprising:

inserting a hollow member in the body, the hollow member having an inner passageway leading to an opening in the hollow member;

moving a pliable fiber through the inner passageway in the hollow member so that the fiber exits the opening in the hollow member;

bending the fiber in a plurality of locations along the length thereof to form a generally ball shaped implant, wherein the bending of the fiber includes contacting an initial end portion of the fiber against tissue in the body, and resisting movement of the fiber with the tissue so that following portions of the fiber bend to form the generally ball shaped implant;

releasing a drug from the generally ball shaped implant; and allowing another end portion of the fiber to extend from the generally ball shaped implant to a location outside of the body and supplying the drug to the implant via the end portion.

25. A method of forming an implant in a body, comprising:

inserting a hollow member in the body, the hollow member having an inner passageway leading to an opening in the hollow member;

moving a pliable fiber through the inner passageway in the hollow member so that the fiber exits the opening in the hollow member;

bending the fiber in a plurality of locations along the length thereof to form a generally ball shaped implant, wherein the bending of the fiber includes contacting an initial portion of the fiber against tissue in the body, and resisting movement of the fiber with the tissue so that following portions of the fiber bend to form the generally ball shaped implant; and releasing one of cells and a cell suspension from the generally ball shaped implant.

26. A method of forming an implant in a body, comprising:

inserting a hollow member in the body, the hollow member having an inner passageway leading to an opening in the hollow member;

moving a pliable fiber through the inner passageway in the hollow member so that the fiber exits the opening in the hollow member; and bending the fiber in a plurality of locations along the length thereof to form a generally ball shaped implant, wherein the bending of the fiber includes contacting an initial portion of the fiber against tissue in the body, and resisting movement of the fiber with the tissue so that following portions of the fiber bend to form the generally ball shaped implant, and wherein the method further comprises forming the generally ball shaped implant in an area of the body to induce tissue growth, and wherein the fiber lacks preformed coiling and the fiber lacks preformed braiding.

27. A method of forming an implant in a body with a device and a fiber in the device, the device including a hollow member having an inner passageway leading to an opening in the hollow member, the method comprising:

inserting the hollow member in the body so that the opening is adjacent to a location at which the implant is to be formed;

flowing fluid through the inner passageway in the hollow member;

transporting the fiber in the flowing fluid through the opening in the hollow member; and contacting the fiber against tissue in the body so that the fiber bends along the length thereof to form a generally ball shaped implant, wherein the fiber lacks preformed coiling and the fiber lacks preformed braiding.

28. The method of claim 27, further comprising storing at least a portion of the fiber in the inner passageway of the hollow member.

29. The method of claim 27, wherein the device includes a housing at a proximal end portion of the hollow member, and wherein the method further comprises storing at least a portion of the fiber in the housing.

30. The method of claim 27, further comprising releasing a drug from the generally ball shaped implant.

31. The method of claim 27, further comprising forming the generally ball shaped implant in a blood vessel to create an embolism.

32. The method of claim 27, further comprising forming the generally ball shaped implant in an area of the body to induce tissue growth.

33. The method of claim 27, further comprising releasing an agent for promoting tissue growth from the generally ball shaped implant.

34. The method of claim 27, further comprising releasing a medication from the generally ball shaped implant.

35. The method of claim 27, further comprising releasing a biologically active substance from the generally ball shaped implant.

36. A method of forming an implant in a body with a device and a fiber in the device, the device including a hollow member having an inner passageway leading to an opening in the hollow member, the method comprising:

inserting the hollow member in the body so that the opening is adjacent to a location at which the implant is to be formed;

flowing fluid through the inner passageway in the hollow member;

transporting the fiber in the flowing fluid through the opening in the hollow member; and contacting the fiber against tissue in the body so that the fiber bends along tie length thereof to form a generally ball shaped implant, wherein the fluid is an adhesive, and wherein the method further comprises stabilizing the generally ball shaped implant with the adhesive.

37. A method of forming an implant in a body with a device and a fiber in the device, the device including a hollow member having an inner passageway leading to an opening in the hollow member, the method comprising:

inserting the hollow member in the body so that the opening is adjacent to a location at which the implant is to be formed;

flowing fluid through the inner passageway in the hollow member;

transporting the fiber in the flowing fluid through the opening in the hollow member; and contacting the fiber against tissue in the body so that the fiber bends along the length thereof to form a generally ball shaped implant, wherein the fluid includes one of a biologically active substance, cells, and a cell suspension, and wherein the method further comprises flowing the fluid in the body via the opening in the hollow member.

38. A method of forming an implant in a body with a device and a fiber in the device, the device including a hollow member having an inner passageway leading to an opening in the hollow member, the method comprising:

inserting the hollow member in the body so that the opening is adjacent to a location at which the implant is to be formed;

flowing fluid through the inner passageway in the hollow member;

transporting the fiber in the flowing fluid through the opening in the hollow member;

contacting the fiber against tissue in the body so that the fiber bends along the length thereof to form a generally ball shaped implant;

releasing a drug from the ball shaped implant; and allowing an end portion of the fiber to extend from the generally ball shaped implant to a location outside of the body and supplying the drug to the implant via the end portion.

39. A method of forming an implant in a body with a device and a fiber in the device, the device including a hollow member having an inner passageway leading to an opening in the hollow member, the method comprising:

inserting the hollow member in the body so that the opening is adjacent to a location at which the implant is to be formed;

flowing fluid through the inner passageway in the hollow member;

transporting the fiber in the flowing fluid through the opening in the hollow member;

contacting the fiber against tissue in the body so that the fiber bends along the length thereof to form a generally ball shaped implant; and allowing an end portion of fiber to extend from the generally ball shaped implant to a location outside of the body and pulling the end portion to remove the implant from the body.

40. A method of forming an implant in a body with a device and a fiber in the device, the device including a hollow member having an inner passageway leading to an opening in the hollow member, the method comprising:

inserting the hollow member in the body so that the opening is adjacent to a location at which the implant is to be formed;

flowing fluid through the inner passageway in the hollow member;

transporting the fiber in the flowing fluid through the opening in the hollow member;

contacting the fiber against tissue in the body so that the fiber bends along the length thereof to form a generally ball shaped implant; and releasing one of cells and a cell suspension from the generally ball shaped implant.

41. A system for introducing a biologically active agent into a body, comprising:

a source of the biologically active agent; and an implant including an elongate fiber having a generally ball shaped portion and an end portion in fluid communication with the source to supply the biologically active agent to the ball shaped portion, the fiber being porous so that the biologically active, agent is capable of being released from the fiber, wherein the fiber is formed of a material including alginate.

42. An implantation system comprising:

a hollow member having a proximal end portion, a distal end portion for insertion into a body, an opening in the distal end portion, and an inner passageway extending from the proximal end portion to the opening in the distal end portion; and an elongate fiber movable in the inner passageway and through the opening of the hollow member, the fiber being formed of a pliable material so that the fiber bends to form a generally ball shaped implant when the fiber contacts body tissue, wherein the fiber is unbiased such that each bend in the ball shaped implant can be formed as movement of the fiber is resisted, the fiber lacks interweaving with other fibers, and the fiber lacks an inner lumen, wherein at least a portion of the fiber includes a plurality of bends, said at least a portion of the fiber being arranged in a generally ball shape.

43. An implantation system comprising:

a hollow member having a proximal end portion, a distal end portion for insertion into a body, an opening in the distal end portion, and an inner passageway extending from the proximal end portion to the opening in the distal end portion; and an elongate fiber movable in the inner passageway and through the opening of the hollow member, the fiber being formed of a pliable material so that the fiber bends to form a generally ball shaped implant when the fiber contacts body tissue, wherein the fiber is unbiased such that each bend in the generally ball shaped implant can be formed as movement of the fiber is resisted, wherein the fiber includes an agent for promoting tissue growth, the agent being capable of being released when the fiber is implanted in the body, and wherein the fiber lacks preformed coiling and the fiber lacks preformed braiding.

44. The system of claim 43, wherein the fiber lacks interweaving with other fibers.

45. An implantation system comprising:

a hollow member having a proximal end portion, a distal end portion for insertion into a body, an opening in the distal end portion, and an inner passageway extending from the proximal end portion to the opening in the distal end portion; and an elongate fiber movable in the inner passageway and through the opening of the hollow member, the fiber being formed of a pliable material so that the fiber bends to form a generally ball shaped implant when the fiber contacts body tissue, wherein the fiber lacks interweaving with other fibers, the fiber has a pliability such that when the fiber is moved in contact with body tissue, the tissue resists movement of the fiber and following portions of the fiber bend to form the generally ball shaped implant, and the fiber is unbiased such that each bend in the ball shaped implant can be formed as movement of the fiber is resisted, wherein the fiber includes a medication capable of being released when the fiber is implanted in the body, and wherein the fiber lacks preformed coiling and the fiber lacks preformed braiding.

46. An implantation system comprising:

a hollow member having a proximal end portion, a distal end portion for insertion into a body, an opening in the distal end portion, and an inner passageway extending from the proximal end portion to the opening in the distal end portion; and an elongate fiber movable in the inner passageway and through the opening of the hollow member, the fiber being formed of a pliable material so that the fiber bends to form a generally ball shaped implant when the fiber contacts body tissue, wherein the fiber lacks interweaving with other fibers, the fiber has a pliability such that when the fiber is moved in contact with body tissue, the tissue resists movement of the fiber and following portions of the fiber bend to form the generally ball shaped implant, and the fiber is unbiased such that each bend in the ball shaped implant can be formed as movement of the fiber is resisted, wherein the fiber includes a biologically active substance capable of being released when the fiber is implanted in the body, and wherein the fiber lacks preformed coiling and the fiber lacks preformed braiding.

47. A method of forming an implant in a body, comprising:

inserting a hollow member in the body, the hollow member having an inner passageway leading to an opening in the hollow member;

moving a pliable fiber through the inner passageway in the hollow member so that the fiber exits the opening in the hollow member;

bending the fiber in a plurality of locations along the length thereof to form a generally ball shaped implant, wherein the bending of the fiber includes contacting an initial portion of the fiber against tissue in the body, and resisting movement of the fiber with the tissue so that following portions of the fiber bend to form the generally ball shaped implant; and releasing an agent for promoting tissue growth from the generally ball shaped implant, wherein the fiber lacks preformed coiling and the fiber lacks preformed braiding.

48. The method of claim 47, wherein the fiber lacks interweaving with other fibers.

49. A method of forming an implant in a body, comprising:

inserting a hollow member in the body, the hollow member having an inner passageway leading to an opening in the hollow member;

moving a pliable fiber through the inner passageway in the hollow member so that the fiber exits the opening in the hollow member, the fiber lacking interweaving with other fibers;

bending the fiber in a plurality of locations along the length thereof to form a generally ball shaped implant, wherein the bending of the fiber includes contacting an initial portion of the fiber against tissue in the body, and resisting movement of the fiber with the tissue so that following portions of the fiber bend to form the generally ball shaped implant; and releasing a medication from the generally ball shaped implant, wherein the fiber lacks preformed coiling and the fiber lacks preformed braiding.

50. A method of forming an implant in a body, comprising:

inserting a hollow member in the body, the hollow member having an inner passageway leading to an opening in the hollow member;

moving a pliable fiber through the inner passageway in the hollow member so that the fiber exits the opening in the hollow member, the fiber lacking interweaving with other fibers;

bending the fiber in a plurality of locations along the length thereof to form a generally ball shaped implant, wherein the bending of the fiber includes contacting an initial portion of the fiber against tissue in the body, and resisting movement of the fiber with the tissue so that following portions of the fiber bend to form the generally ball shaped implant; and releasing a biologically active substance from the generally ball shaped implant, wherein the fiber lacks preformed coiling and the fiber lacks preformed braiding.

51. A method of forming an implant in a body, comprising:

inserting a hollow member in the body, the hollow member having an inner passageway leading to an opening in the hollow member;

moving a pliable fiber through the inner passageway in the hollow member so that the fiber exits the opening in the hollow member, the fiber lacking interweaving with other fibers; and bending the fiber in a plurality of locations along the length thereof to form a generally ball shaped implant, wherein the bending of the fiber includes contacting an initial portion of the fiber against tissue in the body, and resisting movement of the fiber with the tissue so that following portions of the fiber bend to form the generally ball shaped implant, wherein the fiber is formed of a material including alginate.

52. A method of forming an implant in a body with a device and a fiber in the device, the device including a hollow member having an inner passageway leading to an opening in the hollow member, the method comprising:

inserting the hollow member in the body so that the opening is adjacent to a location at which the implant is to be formed;

flowing fluid through the inner passageway in the hollow member;

transporting the fiber in the flowing fluid through the opening in the hollow member; and forming a plurality of bends along the length of the fiber to create a generally ball shaped implant, wherein the fiber lacks preformed coiling and the fiber lacks preformed braiding.

53. An implantation system comprising:
- a hollow member having a proximal end portion, a distal end portion for insertion into a body, an opening in the distal end portion, and an inner passageway extending from the proximal end portion to the opening in the distal end portion; and
- an elongate fiber movable in the inner passageway and through the opening of the hollow member, the fiber being formed of a pliable material so that the fiber bends to form a generally ball shaped implant when the fiber contacts body tissue,
  - wherein the fiber is unbiased such that each bend in the ball shaped implant can be formed as movement of the fiber is resisted, the fiber lacks interweaving with other fibers, and the fiber lacks an inner lumen, and
  - wherein the fiber lacks preformed coiling and the fiber lacks preformed braiding.

54. The implantation system of claim 53, wherein the hollow member is sufficiently flexible to insert the distal end portion of the hollow member through body tissue to a blood vessel leading to a hemangioma.

55. The implantation system of claim 53, further comprising a housing at the proximal end portion of the hollow member, at least a portion of the fiber being stored in the housing prior to formation of the implant.

56. The implantation system of claim 53, wherein at least a portion of the fiber is stored in the hollow member prior to formation of the implant.

57. The implantation system of claim 53, further comprising a coupling at the proximal end portion of the hollow member for placing the inner passageway in fluid communication with a fluid source, the fiber being moved in the passageway and through the opening in the hollow member in response to fluid flow through the inner passageway.

58. The implantation system of claim 53, further comprising a fluid source in fluid communication with the inner passageway, the fiber being moved in the passageway and through the opening in the hollow member in response to fluid flow through the inner passageway.

59. The implantation system of claim 58, wherein the fluid source includes a syringe barrel and a plunger slidable in the syringe barrel to force fluid from the syringe barrel.

60. The implantation system of claim 58, further comprising a pump for pumping fluid from the fluid source to the inner passageway and a valve for controlling flow of the fluid to the inner passageway.

* * * * *

UNITED STATES PATENT AND TRADEMARK OFFICE
CERTIFICATE OF CORRECTION

| | |
|---|---|
| PATENT NO. | : 6,299,590 B1 |
| DATED | : October 9, 2001 |
| INVENTOR(S) | : Patrik Lüscher et al. |

It is certified that error appears in the above-identified patent and that said Letters Patent is hereby corrected as shown below:

Title page,
Item [62], Related U.S. Application Data, change "1997." to -- 1997 (now Pat. No. 6,296,632), which is a 371 of PCT/CH95/00184, filed Aug. 16, 1995. --

Column 1,
Line 5, change "(pending)" to -- (now Pat. No. 6,296,632), which is a 371 of PCT/CH95/00184, filed Aug. 16, 1995. --

Column 10,
Line 59, change "tie" to -- the --.

Column 12,
Line 10, after "agent", delete the comma.

Signed and Sealed this

Twenty-third Day of April, 2002

*Attest:*

JAMES E. ROGAN
*Attesting Officer*     *Director of the United States Patent and Trademark Office*